(12) United States Patent
Cesmeli

(10) Patent No.: US 6,718,004 B2
(45) Date of Patent: Apr. 6, 2004

(54) METHODS AND APPARATUS FOR CORONARY-SPECIFIC IMAGING RECONSTRUCTION

(75) Inventor: Erdogan Cesmeli, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/064,068

(22) Filed: Jun. 6, 2002

(65) Prior Publication Data

US 2003/0002616 A1 Jan. 2, 2003

Related U.S. Application Data

(63) Continuation-in-part of application No. 09/681,944, filed on Jun. 28, 2001, now Pat. No. 6,426,990.

(51) Int. Cl.[7] .............................................. G01N 23/00
(52) U.S. Cl. ............................................ 378/8; 378/62
(58) Field of Search ........................... 378/8, 4, 93, 94, 378/95, 196, 197, 62; 600/427, 425, 407, 428; 382/131, 128

(56) References Cited

U.S. PATENT DOCUMENTS

| | | | |
|---|---|---|---|
| 5,602,891 A | * | 2/1997 | Pearlman ..................... 378/62 |
| 6,370,217 B1 | * | 4/2002 | Hu et al. ...................... 378/8 |
| 6,373,920 B1 | * | 4/2002 | Hsieh ...................... 378/98.11 |
| 6,526,117 B1 | * | 2/2003 | Okerlund et al. ............. 378/8 |
| 6,539,074 B1 | * | 3/2003 | Yavuz et al. ................... 378/4 |

\* cited by examiner

*Primary Examiner*—David V. Bruce
*Assistant Examiner*—Hoon Song
(74) *Attorney, Agent, or Firm*—Robert B. Reeser, III; Armstrong Teasdale LLP

(57) ABSTRACT

A method for imaging a desired coronary artery or desired portion thereof is provided. The method includes reconstructing a first 2D image of a first desired coronary artery branch segment utilizing a first projection dataset acquired during a first desired cardiac phase of a plurality of cardiac cycles to reduce motion artifacts of the first desired coronary artery branch segment, reconstructing a second 2D image of a second desired coronary artery branch segment utilizing a second projection dataset acquired during a second desired cardiac phase of the plurality of cardiac cycles to reduce motion artifacts of the second desired coronary artery branch segment, and reconstructing at least one 3D image of the coronary artery utilizing the first 2D image and the second 2D image.

20 Claims, 5 Drawing Sheets

METHODS AND APPARATUS FOR CORONARY-SPECIFIC IMAGING RECONSTRUCTION

CROSS REFERENCE TO RELATED APPLICATIONS

This application is a Continuation In Part of U.S. patent application Ser. No. 09/681,944 filed Jun. 28, 2001 now U.S. Pat. No. 6,426,990.

BACKGROUND OF INVENTION

This invention relates generally to methods and apparatus for coronary imaging, and more particularly to methods and apparatus for computed tomographic (CT) imaging of specific artery branches with reduced motion artifacts.

Computed tomographic (CT) imaging and magnetic resonance imaging (MRI) can be utilized to visualize coronary arteries, which are very tiny structures. However, visualization of these structures is difficult, because different coronary arteries are subject to different motions throughout a cardiac cycle. For example, the right coronary artery (RCA) remains on a single plane and undergoes large displacements. The left anterior descending (LAD) vessel, on the other hand, lies on a curved surface and its branches follow different motion patterns. Known electrocardiograph (EKG) driven reconstruction methods and apparatus do not take these variations into account, so it has been difficult to achieve optimum visualization of at least some coronary arteries.

SUMMARY OF INVENTION

In one aspect, a method for imaging a desired coronary artery or desired portion thereof utilizing a computed tomography (CT) imaging system is provided. The imaging system includes a rotating gantry, a detector array on the rotating gantry, and a radiation source on the rotating gantry configured to project a beam of radiation towards the detector array through a patient's heart. The method includes scanning a volume of the patient's heart with the CT imaging system to acquire projection data, the volume including at least a first desired coronary artery branch segment and a second desired coronary artery branch segment, and the acquired projection data including a first projection dataset representing the first desired coronary artery branch segment acquired during the first desired cardiac phase of a plurality of cardiac cycles of the patient and a second projection dataset representing the second desired coronary artery branch segment acquired during the second desired cardiac phase of a plurality of cardiac cycles of the patient, and selecting a first cardiac phase corresponding to a low motion period of the first desired coronary artery branch segment of a patient's heart and a different, second cardiac phase corresponding to the second, different desired coronary artery branch segment of the patient's heart. The method also includes reconstructing a first 2D image of the first desired coronary artery branch segment utilizing the first projection dataset acquired during the first desired cardiac phase of a plurality of cardiac cycles to reduce motion artifacts of the first desired coronary artery branch segment, reconstructing a second 2D image of the second desired coronary artery branch segment utilizing the second projection dataset acquired during the second desired cardiac phase of a plurality of cardiac cycles to reduce motion artifacts of the second desired coronary artery branch segment, reconstructing at least one 3D image of the coronary artery utilizing the first 2D image and the second 2D image.

In another aspect, a computed tomography (CT) imaging system having a rotating gantry, a detector array on the rotating gantry, and a radiation source on the rotating gantry configured to project a beam of radiation towards the detector array through a patient's heart is provided. The system is configured to scan a volume of the patient's heart to acquire projection data, the volume including at least a first desired coronary artery branch segment and a second desired coronary artery branch segment, the acquired projection data including a first projection dataset representing the first desired coronary artery branch segment acquired during the first desired cardiac phase of a plurality of cardiac cycles of the patient and the second projection dataset representing the second desired coronary artery branch segment acquired during the second desired cardiac phase of a plurality of cardiac cycles of the patient and select a first cardiac phase corresponding to a low motion period of the first desired coronary artery branch segment of the patient's heart and a different, second cardiac phase corresponding to the second, different desired coronary artery branch segment of the patient's heart. The system is also configured to reconstruct a first 2D image of the first desired coronary artery branch segment utilizing the first projection dataset acquired during the first desired cardiac phase of a plurality of cardiac cycles to reduce motion artifacts of the first desired coronary artery branch segment, reconstruct a second 2D image of the second desired coronary artery branch segment utilizing the second projection dataset acquired during the second desired cardiac phase of a plurality of cardiac cycles to reduce motion artifacts of the second desired coronary artery branch segment, and reconstruct at least one 3D image of the coronary artery utilizing the first 2D image and the second 2D image.

In a further aspect, a machine readable medium having instructions recorded thereon is provided. The machine readable medium is configured to instruct a computer to scan a volume of the patient's heart to acquire projection data, the volume including at least a first desired coronary artery branch segment and a second desired coronary artery branch segment, the acquired projection data including a first projection dataset representing the first desired coronary artery branch segment acquired during the first desired cardiac phase of a plurality of cardiac cycles of the patient and the second projection dataset representing the second desired coronary artery branch segment acquired during the second desired cardiac phase of a plurality of cardiac cycles of the patient and select a first cardiac phase corresponding to a low motion period of the first desired coronary artery branch segment of the patient's heart and a different, second cardiac phase corresponding to the second, different desired coronary artery branch segment of the patient's heart. The machine readable medium is also configured to instruct the computer to reconstruct a first 2D image of the first desired coronary artery branch segment utilizing the first projection dataset acquired during the first desired cardiac phase of a plurality of cardiac cycles to reduce motion artifacts of the first desired coronary artery branch segment, reconstruct a second 2D image of the second desired coronary artery branch segment utilizing the second projection dataset acquired during the second desired cardiac phase of a plurality of cardiac cycles to reduce motion artifacts of the second desired coronary artery branch segment, and reconstruct at least one 3D image of the coronary artery utilizing the first 2D image and the second 2D image.

DETAILED DESCRIPTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) a viewable image. Included among the embodiments generating a viewable image are some that generate a plurality of images, each corresponding to a different z-axis location. Further as used herein, a "segment" of a coronary artery branch is considered as any portion of the branch that is adequately characterized, for image motion artifact reduction purposes, by a single low motion cardiac phase. Thus, it is not impossible that, in some cases, an entire branch may be considered as constituting a single segment.

In addition, as used herein, a "given" or "desired" cardiac phase refers to all or part of a contiguous range of phases around a targeted cardiac phase. The range is such that, were a sufficient number and angular range of views within the range available for a specified portion of the heart, that portion would appear sufficiently stationary such that a substantially artifact-free image could be reconstructed.

Figure 1:
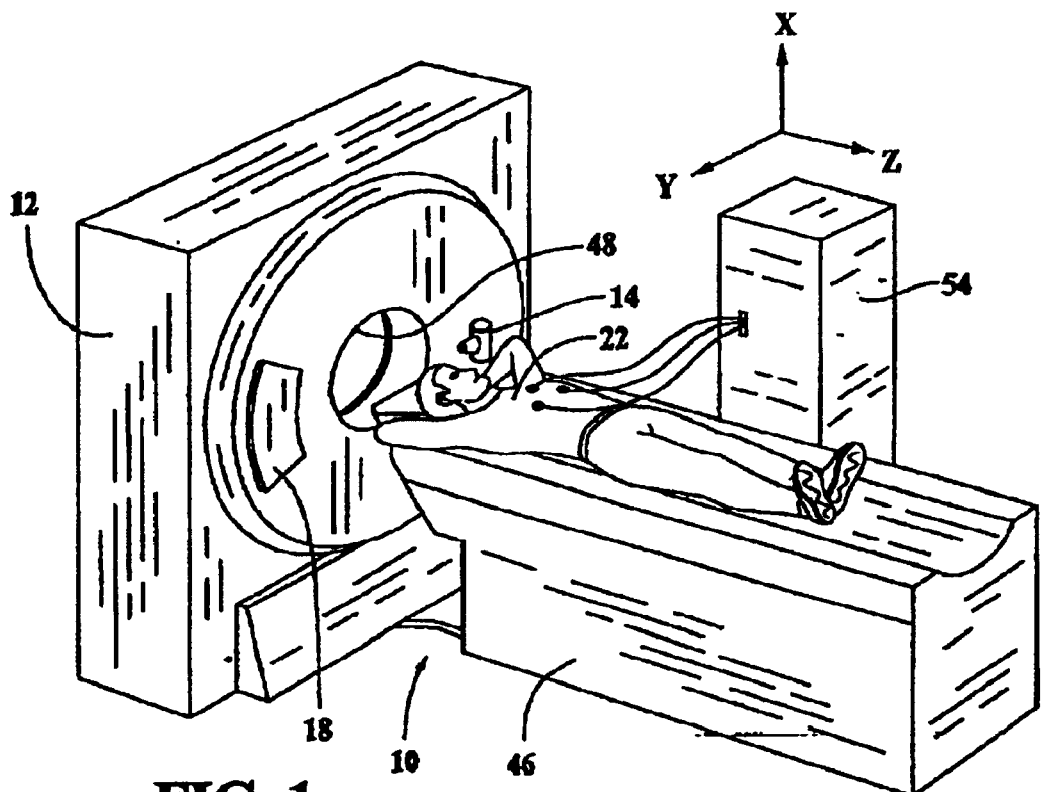
FIG. 1 is a pictorial view of a CT imaging system.
Figure 2:
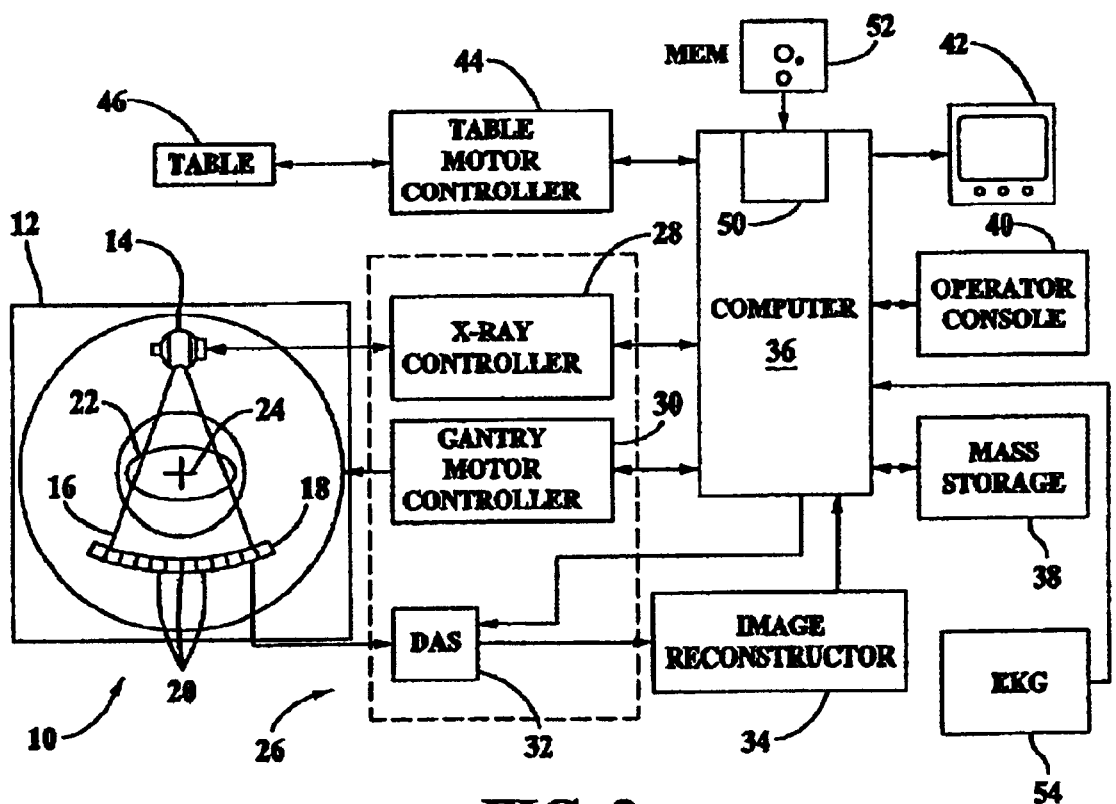
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has at least one x-ray radiation source 14 that projects a beam of x-ray radiation 16 toward a detector array 18 on the opposite side of gantry 12. Radiation beam 16 is, for example, a fan beam, a cone beam, or a parallel beam. Detector array 18 is formed by detector elements 20 that together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. In one embodiment, detector array 18 is fabricated in a multi-slice configuration. In a multi-slice configuration, detector array 18 has a plurality of rows of detector elements or cells 20, only one of which is shown in FIG. 2. One or more additional rows of detector elements 20 in such configurations are arranged parallel to the illustrated row, and each row is transverse to the translation direction of patient 22 (i.e., the z-axis or patient axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In a helical scan as performed in one embodiments of the present invention, table 46 moves while projection data is being collected and gantry 12 is rotating. The "helical pitch" is a measure of the amount of movement of table 46 per rotation of gantry 12.

In one embodiment, computer 36 includes a device 50 for reading and writing onto removable media 52. For example, device 50 is a floppy disk drive, a CD-R/W drive, or a DVD drive. Correspondingly, media 52 is either a floppy disk, a compact disk, or a DVD. Device 50 and media 52 are used in one embodiment to transfer acquired projection data from imaging system 10 to another computer for further processing, or in another embodiment to input machine readable instructions that are processed by computer 36.

Figure 3:
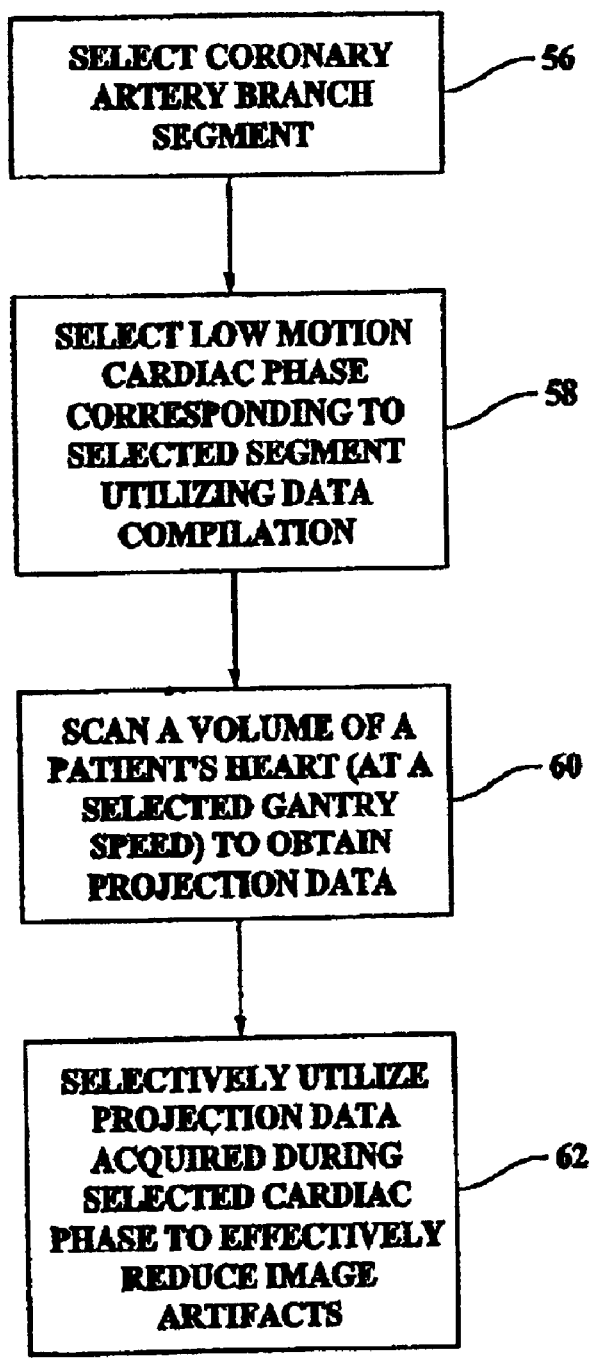
FIG. 3 is a flow chart representative of an embodiment of the present invention.

In one embodiment and referring to FIG. 3, a segment of a coronary artery branch of patient is selected 56 for imaging. A data compilation of coronary artery branch segments and their corresponding low motion cardiac phases is provided. Utilizing this data compilation, a low motion cardiac phase is selected 58 that corresponds to the selected coronary artery branch segment. A volume of the heart of patient 22 is then scanned 60 by imaging system 10 to acquire projection data. The volume scanned includes at least the selected coronary artery branch segment.

To facilitate image reconstruction, a rate of rotation of gantry 12 is set according to the cardiac cycle of the heart of patient 22, or to a measured average cardiac cycle rate. For example, computer 36 is used to detect occurrences of R peaks of an EKG measured by EKG machine 54, shown in FIG. 2. The rotation rate of gantry 12 is selected so that, at the same phase of different cardiac cycles, projection data is acquired from a variety of view angles. Projection data is collected from a sufficient range of view angles to reconstruct an image entirely from projection data acquired at the given cardiac phase. For a helical scan, a multislice detector array is used so that projection data at or near a plane of reconstruction (POR) is acquired by at least one detector row in different cardiac cycles as the scan proceeds.

In one embodiment, the projection data acquired during a scan includes projection data acquired during the selected cardiac phase of a plurality of different cardiac cycles of patient 22. This acquired projection data is used to reconstruct 62 an image of at least the selected coronary artery branch segment. In one embodiment, to effectively reduce motion artifacts of the selected coronary artery branch segment in the reconstructed image, only that projection data acquired during the selected cardiac phase (i.e., the small, contiguous range of phases referred to above) is utilized, to the exclusion of other projection data. Because different portions of the heart undergo minimum displacement velocities at different cardiac phases, the reconstructed image may not be optimized for all parts of the heart appearing in the image in all cases. However, a relatively artifact-free image is obtained of the selected coronary artery.

In another embodiment of the present invention, projection data acquired during the selected cardiac phase is used together with other projection data to reconstruct an image. However, to effectively reduce motion artifacts of the selected coronary artery branch segment in the reconstructed image, weights are applied to the projection data to more heavily weight the projection data acquired during the selected cardiac phase.

Identification and selection of projection data corresponding to a selected cardiac phase is facilitated by the simultaneous recording of an EKG signal from EKG machine 54 during acquisition of the projection data. For example, R peaks in a signal from EKG machine 54 are recorded and located by computer 36, and views of the projection data are tagged with numbers representing cardiac phases as a percentage of time between R peaks.

Although the cardiac periods of patients vary, a rest period of a particular segment of any given artery expressed as a percentage of a cycle type can be expected to be relatively constant. Thus, in one embodiment of the present invention, a data compilation of low motion cardiac phases corresponding to various coronary artery branch segments is derived from observations of a plurality of individuals. For example, low motion phases of a number of coronary arteries in different patients are observed from arteriograms collected from a plurality of individuals. The observed low motion phases (measured, for example, as a percent of a cardiac cycle from the most recent R peak of an EKG signal) are statistically combined, so that, for example, the data compilation contains low motion cardiac phases for each of the different observed cardiac artery branch segments, averaged over the plurality of patients observed. Methods such as those described by Wang et al. ("Cardiac Motion of Coronary Arteries: Variability in the Rest Period and Implications for Coronary MR Angiography," Radiology 1999, 213:751–758) are suitable for assembling a catalog of rest periods for segments of a collection of arteries as a percentage of the R-peak-to-R-peak time of an EKG. The data compilation can include, but does not have to be based upon observations of the patient being scanned. Thus, in one embodiment, the data compilation is based upon observations of a plurality of individuals that exclude observations of patient 22.

Figure 4:
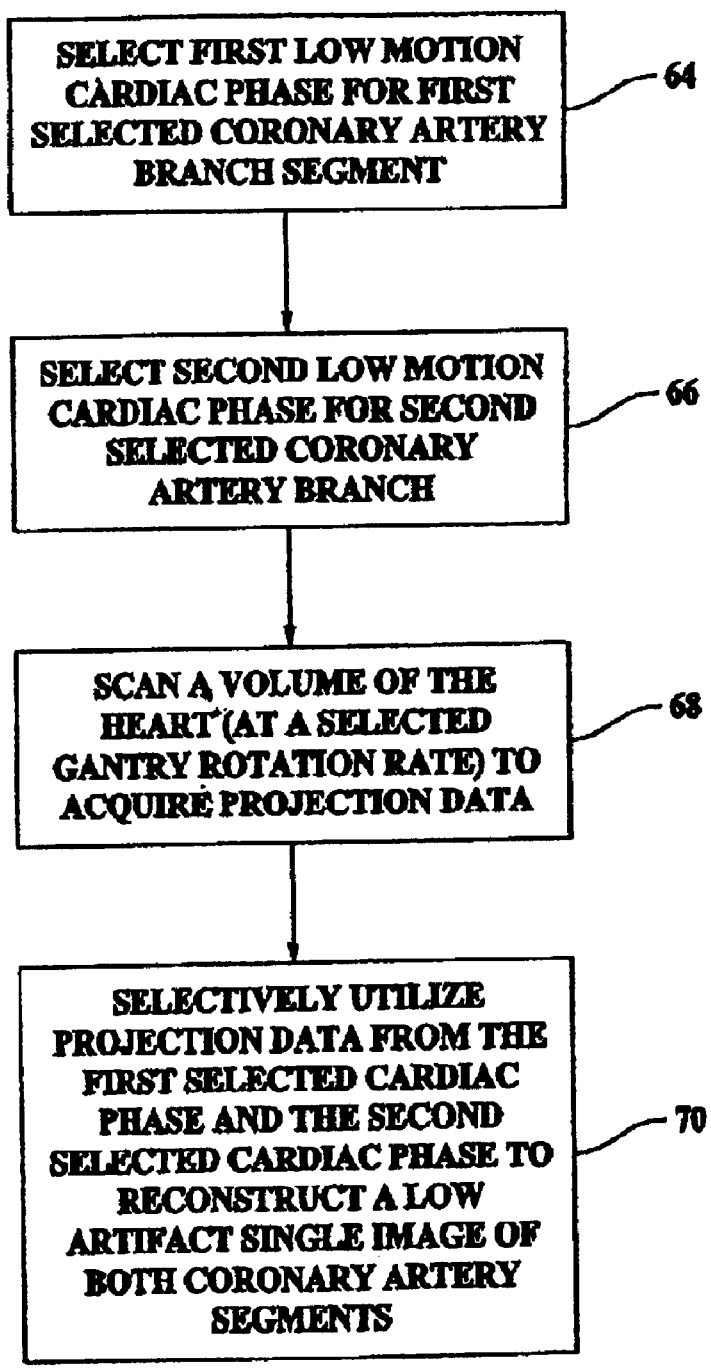
FIG. 4 is a flow chart representative of another embodiment of the present invention in which a composite image of an object is produced.

In some cases, low motion cardiac phases for different segments of the same coronary artery branch or of different coronary artery branches may be the same. In such cases, selection of a single low motion cardiac phase may suffice for artifact-free images of more than a single coronary artery branch segment. However, in some cases, it may be necessary or desirable to produce low artifact images of cardiac artery branch segments that have different low motion cardiac phases. Therefore, in one embodiment of the present invention and referring to FIG. 4, a first cardiac phase corresponding to a low motion period of a first selected coronary artery branch segment of the heart of patient 22 is selected 64. Also, a different, second cardiac phase corresponding to a second, different selected coronary artery branch segment is selected 66. A volume of the heart of patient 22 is scanned 68 using imaging system 10 to acquire projection data. The volume scanned includes at least the first selected coronary artery branch segment and the second selected coronary artery branch segment. Imaging system 10 thus acquires projection data that includes projection data representing the first selected coronary artery branch segment acquired during the first selected cardiac phase of a plurality of cardiac cycles of patient 22. The acquired projection data also includes projection data representing the second selected coronary artery branch segment acquired during the second selected cardiac phase of a plurality of cardiac cycles of patient 22. Using the acquired projection data, a single image including the first coronary artery branch segment and the second coronary artery branch segment of the heart of patient 22 is reconstructed 70.

Figure 5:
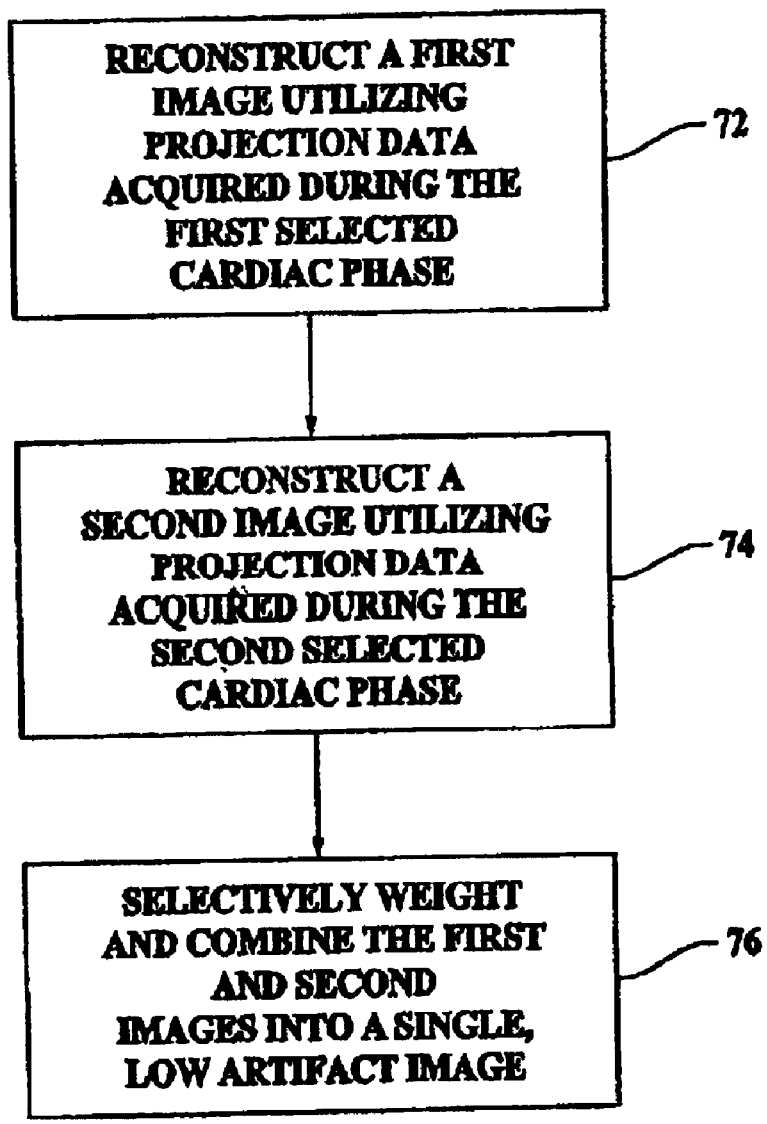
FIG. 5 is a flow chart representative of one technique for selectively utilizing projection data from a first cardiac phase and a second cardiac phase to produce a composite image.

The reconstruction selectively utilizes the projection data acquired during the first selected cardiac phase of a plurality of cardiac cycles to reduce motion artifacts of the first selected coronary artery branch segment on the single image. The reconstruction also selectively utilizes the projection data acquired during the second selected cardiac phase of a plurality of cardiac cycles to reduce motion artifacts of the second selected coronary artery branch segment on the single image. In one embodiment and referring to FIG. 5, the selective utilization of projection data comprises reconstructing 72 a first image including the first selected coronary artery branch segment utilizing projection data obtained only during the first selected cardiac phase of a plurality of cardiac cycles. In addition, a second image is reconstructed 74 including the second selected coronary artery branch segment utilizing projection data obtained only during the second selected cardiac phase of a plurality of cardiac cycles. The first image provides a low motion artifact portion that includes the first selected coronary artery branch segment, and the second image provides a low motion artifact portion that includes the second selected coronary artery branch segment. The two images are selectively weighted and combined 76 (e.g., "morphed") into the single image. The weighting and combining is such that, in a portion of the single image containing the first selected coronary artery branch segment, the contribution of the first image predominates. Similarly, in a portion of the second image containing the second selected coronary artery branch segment, the contribution of the second image predominates. In this manner, motion artifacts of both selected coronary artery branch segments are effectively reduced in the reconstructed single image.

In another embodiment, the projection data is selectively combined by differentially weighting the projection data acquired during the two different selected cardiac phases so that projection data acquired during the first cardiac phase in a plurality of cardiac cycles contributes more heavily in reconstruction to a portion of the image in which the first selected cardiac artery branch segment appears. Similarly, projection data acquired during the second cardiac phase in a plurality of cardiac cycles is weighted so that it contributes more heavily in reconstruction to a portion of the image in which the second selected cardiac artery branch segment appears.

Figure 6:
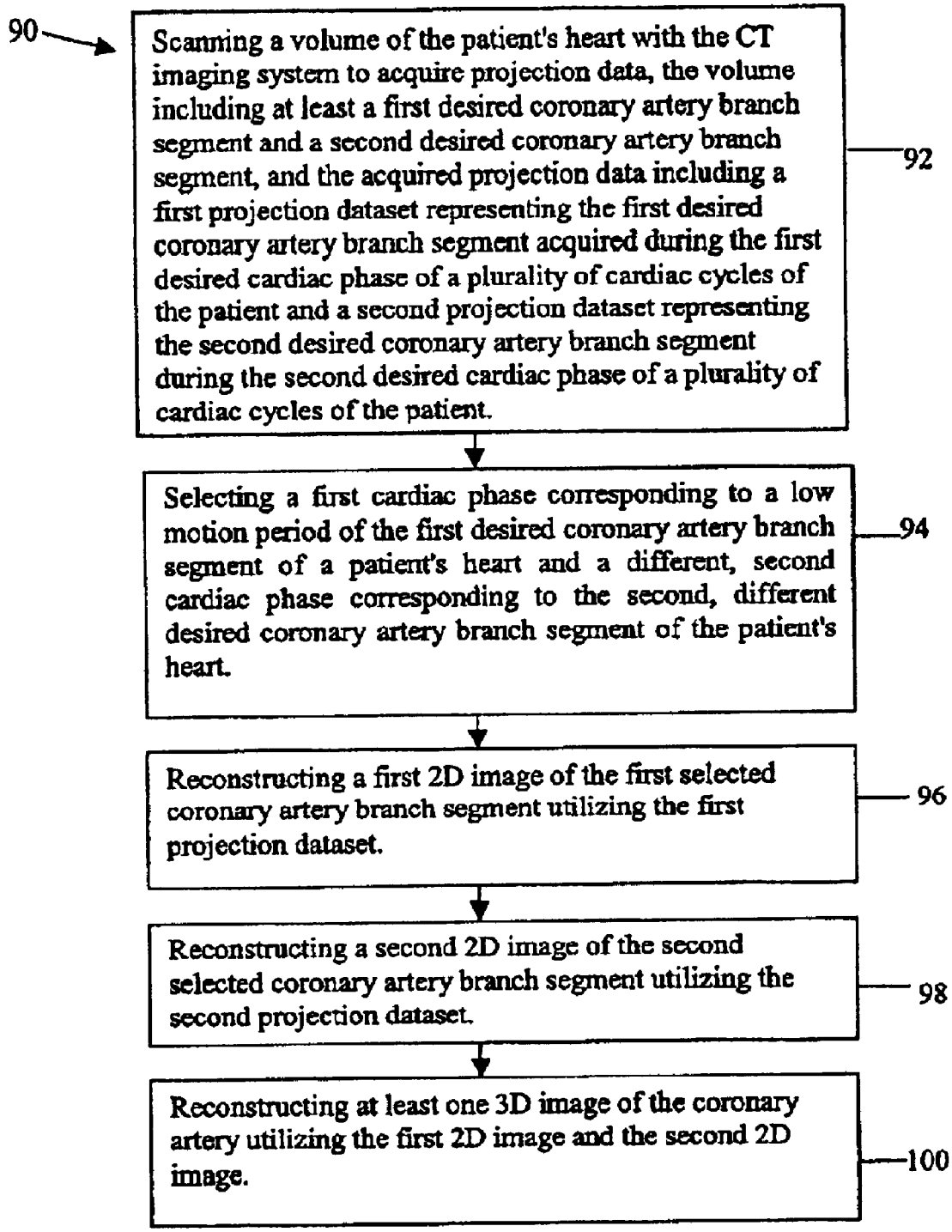
FIG. 6 is a flow chart representative of another embodiment of the present invention in which a composite image of an object is produced.

FIG. 6 is a method 90 for imaging a desired coronary artery or selected portion thereof. Method 90 includes, scanning 92 a volume of the patient's heart with CT imaging system 10 to acquire projection data, the volume including at least a first selected coronary artery branch segment and a second selected coronary artery branch segment, and the acquired projection data including a first projection dataset representing the first selected coronary artery branch segment acquired during the first selected cardiac phase of a plurality of cardiac cycles of the patient and a second projection dataset representing the second selected coronary artery branch segment acquired during the second selected cardiac phase of a plurality of cardiac cycles of the patient, and selecting 94 a first cardiac phase corresponding to a low motion period of the first selected coronary artery branch segment of a patient's heart and a different, second cardiac phase corresponding to the second, different selected coronary artery branch segment of the patient's heart. Method 60 also includes reconstructing 96 a first 2D image of the first selected coronary artery branch segment utilizing the first projection dataset acquired during the first selected cardiac phase of a plurality of cardiac cycles to reduce motion artifacts of the first selected coronary artery branch segment, reconstructing 98 a second 2D image of the second selected coronary artery branch segment utilizing the second projection dataset acquired during the second selected cardiac phase of a plurality of cardiac cycles to reduce motion artifacts of the second selected coronary artery branch segment, and reconstructing 100 at least one 3D image of the coronary artery utilizing the first 2D image and the second 2D image.

In an alternative embodiment, method 90 includes selecting 92 a first cardiac phase corresponding to a low motion period of a first selected coronary artery branch segment of a patient's heart and a different, second cardiac phase corresponding to a second, different selected coronary artery branch segment of the patient's heart, and scanning 94 a volume of the patient's heart with CT imaging system 10 to acquire projection data, the volume including at least the first selected coronary artery branch segment and the second selected coronary artery branch segment, and the acquired projection data including a first projection dataset representing the first selected coronary artery branch segment acquired during the first selected cardiac phase of a plurality of cardiac cycles of the patient and a second projection dataset representing the second selected coronary artery branch segment acquired during the second selected cardiac phase of a plurality of cardiac cycles of the patient.

As described herein, for each cardiac segment, a different cardiac phase can be utilized to generate a plurality of 2D images representative of the plurality of artery branch segments at different phases. The plurality of 2D images are then combined to form a single 3D image representative of the coronary artery branch. For example, a first cardiac phase corresponding to a low motion period of a first desired coronary artery branch segment is used to reconstruct a first 2D image. A second cardiac phase corresponding to a low motion period of a second desired coronary artery branch segment is used to reconstruct a second 2D image of a patient's heart, and a third cardiac phase corresponding to a low motion period of a third desired coronary artery branch segment is used to reconstruct a third 2D image. The first 2D image of the first segment, the second 2D image of the second segment, and the third 2D image of the third segment are then combined to generate a single 3D image of the artery (i.e. all the segments combined). As described herein a plurality of 2D images of a plurality of segments are combined to form a 3D image. Also, as described herein the plurality of segments may include segments acquired during the same cardiac phase.

Method 90 facilitates allowing the operator to select the best segment, i.e. selecting the best phase or the low motion phase to reconstruct the 3D image of the coronary artery. The additional steps that are added to the above-described embodiments to extend their applicability to images having three or more selected coronary artery branch segments should, by now, be apparent to those skilled in the art. In general, an additional coronary artery phase is selected for each additional selected coronary artery branch segment.

Computer 36 and/or image reconstructor 34 of imaging system 10, either alone or in combination, provide the processing power necessary to perform the computational steps described above in at least one embodiment of the present invention. Instructions for performing the computational steps and the compilation of low motion cardiac phases corresponding to different coronary artery branch segments are stored in an associated memory, such as mass storage device 38, read only or read/write memory (not shown separately in FIG. 1), or media 52.

In at least one embodiment of the present invention, a computer system separate from imaging system 10 (for example, a workstation, not shown in the figures) is provided to reconstruct images using projection data acquired by imaging system 10. In these embodiments, acquired projection data and corresponding cardiac phase information is transferred from imaging system 10 to the separate computer system via a network (not shown) or suitable media 52. As a free-standing, separate computer system, these embodiments do not require a rotating gantry, a radiation source, or a detector array of their own. Also, these embodiments are configured to read or input projection data previously acquired by a CT imaging system. In other ways, they are configured in manners similar to the other apparatus embodiments discussed herein.

Other embodiments of the present invention include machine-readable media 52 having recorded thereon instructions configured to instruct a computer system to perform steps of one or more of the methods described herein.

The above-described embodiments will be recognized as achieving improved visualization of selected coronary artery branch segments as compared to known methods. Moreover, some of the above-described embodiments take into account variations in motion patterns between different coronary artery branch segments in a single image. These embodiments provide simultaneously improved visualization for both segments in a single image.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. However, many other CT systems including "fourth generation" systems wherein the detector is a full-ring or partial-ring stationary detector and an x-ray source could rotate with the gantry or includes distributed sources along a ring, along a line, or over an area, may be used. While the invention has been described in terms of various specific embodiments, those skilled in the art will recognize that the invention can be practiced with modification within the spirit and scope of the claims.

What is claimed is:

1. A method for imaging a desired coronary artery or desired portion thereof utilizing a computed tomography (CT) imaging system comprising a rotating gantry, a detector array on the rotating gantry, and a radiation source on the rotating gantry configured to project a beam of radiation towards the detector array through a patient's heart; said method comprising:

scanning a volume of the patient's heart with the CT imaging system to acquire projection data, the volume including at least a first desired coronary artery branch segment and a second desired coronary artery branch segment, and the acquired projection data including a first projection dataset representing the first desired coronary artery branch segment acquired during a first desired cardiac phase of a plurality of cardiac cycles of the patient and a second projection dataset representing the second desired coronary artery branch segment acquired during a second desired cardiac phase of a plurality of cardiac cycles of the patient;

selecting the first cardiac phase corresponding to a low motion period of the first desired coronary artery branch segment of a patient's heart and selecting the second cardiac phase corresponding to a low motion period of the second desired coronary artery branch segment of a patient's heart;

reconstructing a first 2D image of the first desired coronary artery branch segment utilizing the first projection dataset acquired during the first desired cardiac phase of a plurality of cardiac cycles to reduce motion artifacts of the first desired coronary artery branch segment;

reconstructing a second 2D image of the second desired coronary artery branch segment utilizing the second projection dataset acquired during the second desired cardiac phase of a plurality of cardiac cycles to reduce motion artifacts of the second desired coronary artery branch segment;

reconstructing at least one 3D image of the coronary artery utilizing the first 2D image and the second 2D image.

2. A method in accordance with claim 1 wherein said reconstructing at least one 3D image including the first desired coronary artery branch segment and the second desired coronary artery branch segment comprises reconstructing a first 2D image excluding projection data other than the first projection dataset acquired during the first selected cardiac phase of a plurality of cardiac cycles and a second 2D image excluding projection data other than the second projection dataset acquired during the second desired cardiac phase of a plurality of cardiac cycles, and combining the first 2D image and the second 2D image to effectively reduce motion artifacts of both the first desired coronary artery and the second desired coronary artery in the generated 3D image.

3. A method in accordance with claim 1 wherein said reconstructing at least one 3D image including the first desired coronary artery branch segment and the second desired coronary artery branch segment comprises selectively utilizing the first projection dataset acquired during the first desired cardiac phase of a plurality of cardiac cycles and the second projection dataset acquired during the second desired cardiac phase of a plurality of cardiac cycles in reconstruction to effectively reduce motion artifacts of both the first desired coronary artery and the second desired coronary artery in the 3D image.

4. A computed tomography (CT) imaging system having a rotating gantry, a detector array on said rotating gantry, and a radiation source on said rotating gantry configured to project a beam of radiation towards said detector array through a patient's heart; said system configured to:

scan a volume of a patient's heart to acquire projection data, the volume including at least a first desired coronary artery branch segment and a second desired coronary artery branch segment, said acquired projection data including a first projection dataset representing said first desired coronary artery branch segment acquired during a first desired cardiac phase of a plurality of cardiac cycles of the patient and said second projection dataset representing a second desired coronary artery branch segment acquired during the second desired cardiac phase of a plurality of cardiac cycles of the patient;

utilize a data compilation of low motion cardiac phases and corresponding coronary artery branch segments to select the first cardiac phase corresponding to the desired first coronary artery branch segment;

utilize a data compilation of low motion cardiac phases and corresponding coronary artery branch segments to select the second cardiac phase corresponding to the desired second coronary artery branch segment;

reconstruct a first 2D image of said first desired coronary artery branch segment utilizing said first projection dataset acquired during the first desired cardiac phase of a plurality of cardiac cycles to reduce motion artifacts of the first desired coronary artery branch segment;

reconstruct a second 2D image of said second desired coronary artery branch segment utilizing said second projection dataset acquired during the second desired cardiac phase of a plurality of cardiac cycles to reduce motion artifacts of the second desired coronary artery branch segment; and reconstruct at least one 3D image of the coronary artery utilizing the first 2D image and the second 2D image.

5. A system in accordance with claim 4 wherein to reconstruct a 3D image of the volume of the patient's heart, said system is configured to reconstruct said image without utilizing projection data other than said projection data acquired during said desired cardiac phase of the plurality of cardiac cycles.

6. A system in accordance with claim 4 wherein said data compilation of low motion cardiac phases and corresponding coronary artery branch segments is a data compilation derived from observations of a plurality of individuals.

7. A system in accordance with claim 6 wherein said data compilation is derived solely from individuals other than the patient.

8. A computed tomographic (CT) imaging for acquiring views of an object, said CT system comprising:

a rotating gantry;

a detector array on the rotating gantry;

at least one radiation source on the rotating gantry; and a computer coupled to said detector array and said radiation source, said computer configured to:

scan a volume of the patient's heart to acquire projection data, the volume including at least a first desired coronary artery branch segment and a second different desired coronary artery branch segment, the acquired projection data including a first projection dataset representing the first desired coronary artery branch segment acquired during a first desired cardiac phase of a plurality of cardiac cycles of the patient and a second projection dataset representing the second desired coronary artery branch segment acquired during a second desired cardiac phase of a plurality of cardiac cycles of the patient;

select the first cardiac phase corresponding to a low motion period of the first desired coronary artery branch segment of the patient's heart and select the second cardiac phase corresponding to a low motion period of the second desired coronary artery branch segment of the patient's heart;

reconstruct a first 2D image of the first desired coronary artery branch segment utilizing the first projection dataset acquired during the first desired cardiac phase of a plurality of cardiac cycles to reduce motion artifacts of the first desired coronary artery branch segment;

reconstruct a second 2D image of the second desired coronary artery branch segment utilizing the second projection dataset acquired during the second desired cardiac phase of a plurality of cardiac cycles to reduce motion artifacts of the second desired coronary artery branch segment; and reconstruct at least one 3D image of the coronary artery utilizing the first 2D image and the second 2D image.

9. A system in accordance with claim 8 wherein to reconstruct at least one 3D image including the first desired coronary artery branch segment and the second desired coronary artery branch segment, said computer is configured to reconstruct a first 2D image excluding projection data other than the projection data acquired during the first desired cardiac phase of a plurality of cardiac cycles and a second 2D image excluding projection data other than the projection data acquired during the second desired cardiac phase of a plurality of cardiac cycles, and combine the first 2D image and the second 2D image to effectively reduce motion artifacts of both the first desired coronary artery and the second desired coronary artery in the single 3D image.

10. A system in accordance with claim 8 wherein to reconstruct at least one 3D image including the first desired coronary artery branch segment and the second desired coronary artery branch segment, said computer is configured to selectively utilize the first projection dataset acquired during the first desired cardiac phase of a plurality of cardiac cycles and the projection data dataset acquired during the second desired cardiac phase of a plurality of cardiac cycles in reconstruction to effectively reduce motion artifacts of both the first desired coronary artery and the second desired coronary artery in the single 3D image.

11. A computer system configured to:

utilize a data compilation of low motion cardiac phases and corresponding coronary artery branch segments to select a first cardiac phase corresponding to a desired first coronary artery branch segment;

utilize a data compilation of low motion cardiac phases and corresponding coronary artery branch segments to select a second cardiac phase corresponding to a desired second coronary artery branch segment;

read projection data acquired by a computed tomographic (CT) imaging system during a scan of a volume of a patient's heart, the volume including at least the first desired coronary artery branch segment and the second coronary artery branch segment, the acquired projection data including the first projection dataset and the second projection dataset; and reconstruct a first 2D image of the first desired coronary artery branch segment utilizing the first projection dataset acquired during the first desired cardiac phase of a plurality of cardiac cycles to reduce motion artifacts of the first desired coronary artery branch segment;

reconstruct a second 2D image of the second desired coronary artery branch segment utilizing the second projection dataset acquired during the second desired cardiac phase of a plurality of cardiac cycles to reduce motion artifacts of the second desired coronary artery branch segment; and reconstruct at least one 3D image of the coronary artery utilizing the first 2D image and the second 2D image.

12. A computer system in accordance with claim 11 wherein to reconstruct a 3D image of the volume of the patient's heart, said computer system is configured to reconstruct the image without utilizing projection data other than the projection data acquired during the first desired cardiac phase of the plurality of cardiac cycles and the second desired cardiac phase.

13. A computer system in accordance with claim 11 wherein said data compilation of low motion cardiac phases and corresponding coronary artery branch segments is a data compilation derived from observations of a plurality of individuals.

14. A computer system in accordance with claim 13 wherein said data compilation is derived solely from individuals other than the patient.

15. A computer system configured to:

scan a volume of the patient's heart to acquire projection data, the volume including at least a first desired coronary artery branch segment and a second desired coronary artery branch segment, the acquired projection data including a first projection dataset representing the first desired coronary artery branch segment acquired during a first desired cardiac phase of a plurality of cardiac cycles of the patient and the second projection dataset representing the second desired coronary artery branch segment acquired during a second desired cardiac phase of a plurality of cardiac cycles of the patient;

select the first cardiac phase corresponding to a low motion period of the first desired coronary artery branch segment of the patient's heart and select the second cardiac phase corresponding to a low motion period of the second desired coronary artery branch segment of the patient's heart;

reconstruct a first 2D image of the first desired coronary artery branch segment utilizing the first projection dataset acquired during the first desired cardiac phase of a plurality of cardiac cycles to reduce motion artifacts of the first desired coronary artery branch segment;

reconstruct a second 2D image of the second desired coronary artery branch segment utilizing the second projection dataset acquired during the second desired cardiac phase of a plurality of cardiac cycles to reduce motion artifacts of the second desired coronary artery branch segment; and reconstruct at least one 3D image of the coronary artery utilizing the first 2D image and the second 2D image.

16. A computer system in accordance with claim 15 wherein to reconstruct the 3D image including the first desired coronary artery branch segment and the second coronary artery branch segment, said computer system is configured to reconstruct a first 2D image excluding projection data other than the first projection dataset acquired during the first desired cardiac phase of a plurality of cardiac cycles and a second 2D image excluding projection data other than the second projection dataset acquired during the second desired cardiac phase of a plurality of cardiac cycles, and combine the first 2D image and the second 2D image to effectively reduce motion artifacts of both the first desired coronary artery and the second desired coronary artery in the single 3D image.

17. A computer system in accordance with claim 16 wherein to reconstruct said 3D image including the first desired coronary artery branch segment and the second desired coronary artery branch segment, said computer system is configured to selectively utilize the first projection dataset acquired during the first desired cardiac phase of a plurality of cardiac cycles and the second projection dataset acquired during the second desired cardiac phase of a plurality of cardiac cycles in reconstruction to effectively reduce motion artifacts of both the first desired coronary artery and the second desired coronary artery in the single 3D image.

18. A machine readable medium having instructions recorded thereon configured to instruct a computer to:

scan a volume of the patient's heart to acquire projection data, the volume including at least a first desired coronary artery branch segment and a second desired coronary artery branch segment, said acquired projection data including a first projection dataset representing the first desired coronary artery branch segment acquired during the first desired cardiac phase of a plurality of cardiac cycles of the patient and said second projection dataset representing the second desired coronary artery branch segment acquired during the second desired cardiac phase of a plurality of cardiac cycles of the patient;

select a first cardiac phase corresponding to a low motion period of the first desired coronary artery branch segment of the patient's heart and a different, second cardiac phase corresponding to the second, different desired coronary artery branch segment of the patient's heart;

reconstruct a first 2D image of the first desired coronary artery branch segment utilizing the first projection dataset acquired during the first desired cardiac phase of a plurality of cardiac cycles to reduce motion artifacts of the first desired coronary artery branch segment;

reconstruct a second 2D image of the second desired coronary artery branch segment utilizing the second projection dataset acquired during the second desired cardiac phase of a plurality of cardiac cycles to reduce motion artifacts of the second desired coronary artery branch segment; and reconstruct at least one 3D image of the coronary artery utilizing the first 2D image and the second 2D image.

19. A machine readable medium in accordance with claim 18 wherein to reconstruct said at least one 3D image including the first desired coronary artery branch segment and the second desired coronary artery branch segment, said machine readable medium has recorded thereon instructions configured to instruct the computer to reconstruct a first 2D image excluding projection data other than the first projection dataset acquired during the first desired cardiac phase of a plurality of cardiac cycles and a second 2D image excluding projection data other than the second projection dataset acquired during the second desired cardiac phase of a plurality of cardiac cycles, and combine the first 2D image and the second 2D image to effectively reduce motion artifacts of both the first desired coronary artery and the second desired coronary artery in the 3D image.

20. A machine readable medium in accordance with claim 18 wherein to reconstruct said at least one 3D image including the first desired coronary artery branch segment and the second desired coronary artery branch segment, said machine readable medium has recorded thereon instructions configured to instruct the computer to selectively utilize the first projection dataset acquired during the first desired cardiac phase of a plurality of cardiac cycles and the second projection dataset acquired during the second desired cardiac phase of a plurality of cardiac cycles in reconstruction to effectively reduce motion artifacts of both the first desired coronary artery and the second desired coronary artery in the 3D image.

\* \* \* \* \*